(12) United States Patent
Silberg (10) Patent No.: US 6,565,521 B1
(45) Date of Patent: May 20, 2003

(54) SYSTEM AND METHOD OF VESSEL REMOVAL

(76) Inventor: Barry N. Silberg, 1818 Morley Way, Santa Rosa, CA (US) 95404

( * ) Notice: Subject to any disclaimer, the term of this patent is extended or adjusted under 35 U.S.C. 154(b) by 25 days.

(21) Appl. No.: 10/000,739

(22) Filed: Nov. 30, 2001

(51) Int. Cl.[7] .................................................. A61H 1/00

(52) U.S. Cl. ............................... 601/2; 606/1; 600/36; 607/105

(58) Field of Search ..................... 606/1; 601/2; 600/36; 607/96, 99, 105

(56) References Cited

U.S. PATENT DOCUMENTS

| 5,884,631 A | 3/1999 | Silberg ........................ 128/898 |
| 5,928,138 A | 7/1999 | Knight et al. ................ 600/201 |
| 5,980,549 A | 11/1999 | Chin ............................ 606/190 |
| 6,039,048 A | 3/2000 | Silberg ........................ 128/808 |
| 6,228,082 B1 * | 5/2001 | Baker et al. .................. 606/49 |
| 6,277,137 B1 | 8/2001 | Chin ............................ 606/190 |

OTHER PUBLICATIONS

E. Solarte, et al., Erchonia Lasers—The Future of Liposuction: Effects of The Irradiation With Laser Light in the Phantoms of Transmission of Dissolutions of Adiposcytes II, Majes–Tec Innovations, Inc.

* cited by examiner

Primary Examiner—Francis J. Jaworski
Assistant Examiner—Barry Pass
(74) Attorney, Agent, or Firm—Susan M. Schmitt (57) ABSTRACT

A method and system for removing body vessels from a patient is provided. An embodiment of the method includes a method for harvesting a vessel for subsequent use in a grafting procedure, such as, for example, saphenous vein graft harvesting for a coronary bypass surgical operation. A quantity of a solution is infused into tissue surrounding the portion of the vessel to be removed. An external device is used to apply an energy field to the tissue to loosen the intercellular connections between the tissue and the vessel to be removed. One such device is an ultrasonic instrument having an ultrasonic transducer comprised of a composite of ultrasonic crystal transducers. Once the energy field has been applied, the portion of the vessel to be removed is separated from surrounding tissue and tributary vessels are ligated. The portion of the vessel is then transected and removed from the body.

23 Claims, 7 Drawing Sheets

SYSTEM AND METHOD OF VESSEL REMOVAL

FIELD OF THE INVENTION

The present invention relates to removal or harvesting of body vessels, and, in one application, to a device and method for assisting in a saphenous vein graft harvesting procedure.

BACKGROUND OF THE INVENTION

Vessels have been removed from patients for various reasons. Diseased varicose veins have been removed, typically from a patient's legs. Vessels have been harvested to provide a vessel graft. In one common procedure, saphenous veins are harvested for use as a vessel graft to bypass clogged coronary arteries.

The saphenous vein is located within a subcutaneous layer along a patient's inner thigh to the lower limb. In saphenous vein graft harvesting for coronary artery bypass procedures, the saphenous vein is removed from the patient and used as a graft to bypass occluded arteries. Saphenous veins graft harvesting has been accomplished in both open and endoscopic procedures. In an open procedure, typically a long incision is made along the inner thigh from the groin to the knee and possibly along the lower portion of the leg as well. The main vessel is ligated and various tributary vessels along the length of the vessel are ligated. The vessel is separated or dissected away from surrounding tissue, which may include fibrous tissue and connective tissue. Various cutting, dissecting and tissue separating instruments may be used for this purpose. After ligating and separating the vessel, it is transected and removed and prepared for use as a graft. In the open procedures, saphenous vein graft harvesting is highly traumatic and invasive, causing significant, and frequently persistent, post operative pain, and requiring significant time for recovery. Wound break down, infections and other complications commonly result from the saphenous vein graft harvesting. It is believed that some of the reasons for complications in such procedures are, the length of the incision, the dehydration of the subcutaneous fatty layer from prolonged exposure to air during dissection of the vessel, the density of the tissue requiring significant dissection, and the already debilitated status of many of the patents.

Endoscopic techniques have been developed to reduce trauma from the incision. The endoscopic procedures, like the open procedures, also strive to ligate the main vessel and its tributaries and to separate the vessel from surrounding tissue before removing the vessel. An incision is made on the inner thigh near the knee, and the saphenous vein is identified and isolated. In one procedure, the area along the vessel is insufflated with a gas such as CO2, and using a blunt tip trocar, to provide a working area. Other instruments and procedures have been proposed to provide such working space and to further separate the vein from surrounding tissue. Such instruments and procedures have included, for example, initially using an optical dissector, other blunt dissector or cannula to dissect or separate tissue from the superior surface of the vein. Then, e.g., using a balloon expandable member to further separate tissue, or using an optical retractor to retract dissected tissue away from the superior surface of the vessel, additional subcutaneous space is created. Typically, endoscopically guided instruments are used to separate the vein from surrounding tissue as the instruments are maneuvered along the length of the vein while side branches or tributaries of the vein are dissected, ligated and then transected to permit removal of the vein. The endoscopic procedure in general, entails using some form of visualization of the procedure that is performed through small incisions. However, because of the dense nature of the subcutaneous tissues in this area in many people, the tissue separation can be difficult, leading to bleeding that further restricts visualization in the procedure, and tissue trauma and bruising including injury to the vessel making it less suitable as a graft. Due to the denseness of the tissue, along with the resulting difficulty in maneuvering and visualizing the procedure, endoscopic harvesting has had limited success and frequently during such procedure, the endoscopic instruments are abandoned and the surgeon will resort to an open procedure.

Accordingly it would be desirable to provide instruments and methods for removing vessels and in particular for saphenous vein graft harvesting in either an open or endoscopic procedure that reduce tissue trauma, provide easier separation of the vein from the surrounding tissue, and improve recovery.

SUMMARY OF THE INVENTION

A method and system for removing body vessels from a patient is provided. An embodiment of the method includes a method for harvesting a vessel for subsequent use in a grafting procedure, such as, for example, saphenous vein graft harvesting for a coronary bypass surgical operation. According to on embodiment, a quantity of a solution is infused into tissue surrounding the portion of the vessel to be removed. An external device is used to apply an energy field to the tissue to loosen the intercellular connections between the tissue and the vessel to be removed. One such device is an ultrasonic instrument having an ultrasonic transducer comprised of a composite of ultrasonic crystal transducers. Once the energy field has been applied, the portion of the vessel to be removed is separated from surrounding tissue and tributary vessels are ligated. The portion of the vessel is then transected and removed from the body. It is believed that the procedure will be less traumatic by decreasing time required to perform the dissection and ligation portions of the procedure and by decreasing bleeding, tissue tearing, post operative pain and complications.

One embodiment of the present invention provides a system and method for preparing the fibrous and connective tissue surrounding the vessel by warming and softening the tissue using an externally applied energy source directed through the skin to the surgical site, in combination with infusing a solution in the tissue surrounding the surgical site. It is believed the procedure will decrease bleeding and minimize bruising and tissue trauma. The procedure of the present invention is particularly suitable for removing vessels that lie within the subcutaneous tissue layer. In one embodiment, the procedure is used for saphenous vein graft harvesting.

According to an embodiment of the invention, the skin tissue is initially prepared by infusing a solution of normal saline that has been mixed with a small amount of lidocaine and epinephrine under the skin in a subcutaneous layer. An external ultrasound device is used to apply ultrasonic energy to the skin for approximately around 2–5 minutes. The ultrasonic energy loosens the layer of skin and surrounding tissue permitting easier passage of surgical instruments and improving the accuracy as well as the ease and efficiency. Once the tissue has been infused and the energy applied, in an open or endoscopic procedure, the vessel is then separated from the surrounding tissue; ligated (including from all the tributary vessels); and transected from the remaining vessels and tributaries. The vessel is then removed. Known surgical techniques may be used for tissue separation, dissection, ligation and transection.

It is believed that the ultrasonic energy as applied will loosen intercellular connections, i.e., connections between the vessel and surrounding tissue whether it be connective tissue of e.g., fibrous tissue held by hydrostatic pressure. The infused fluid acts as a medium through which the ultrasonic energy can place a field around the vessel and attenuate to some degree, the ultrasonic energy and possible resulting tissue damage. It is believed that through cavitation and microstreaming (i.e., movement of the fluid in a linear direction away from the ultrasonic energy source), intracellular connections are loosened, tissue viscosity is decreased, and the tissue becomes super hydrated with minimal destruction of cells allowing dissection to proceed much more easily. Additional benefits provide better viewing of the surgical site due to reduced bleeding from tearing of dense tissue surrounding the vessel and tributaries from the main vessel. In an open technique, superhydrating the tissues reduces the undesired effects of tissue dehydration during the open procedure whether initially performed as an open procedure or where the endoscopic procedure is abandoned in favor of an open procedure. By infusing fluid in an applying the energy, fluid is infused into subcutaneous interstitial space.

The procedure described herein may be used in other applications other than saphenous vein graft harvesting or vessel harvesting. The procedure, for example, may be used to remove diseased veins such as varicose veins.

Other energy forms may be used other than ultrasonic energy to achieve a desired result. The energy may be in the form of other acoustic waves or mechanical pressure waves. The energy may also be in the form of electromagnetic energy, e.g., columnated light or a low level laser such as an Erchonia™ laser device. Other energies that translate into a kinetic energy in the infused solution with minimal damage to surrounding tissue may be used.

DETAILED DESCRIPTION

Figure 1:
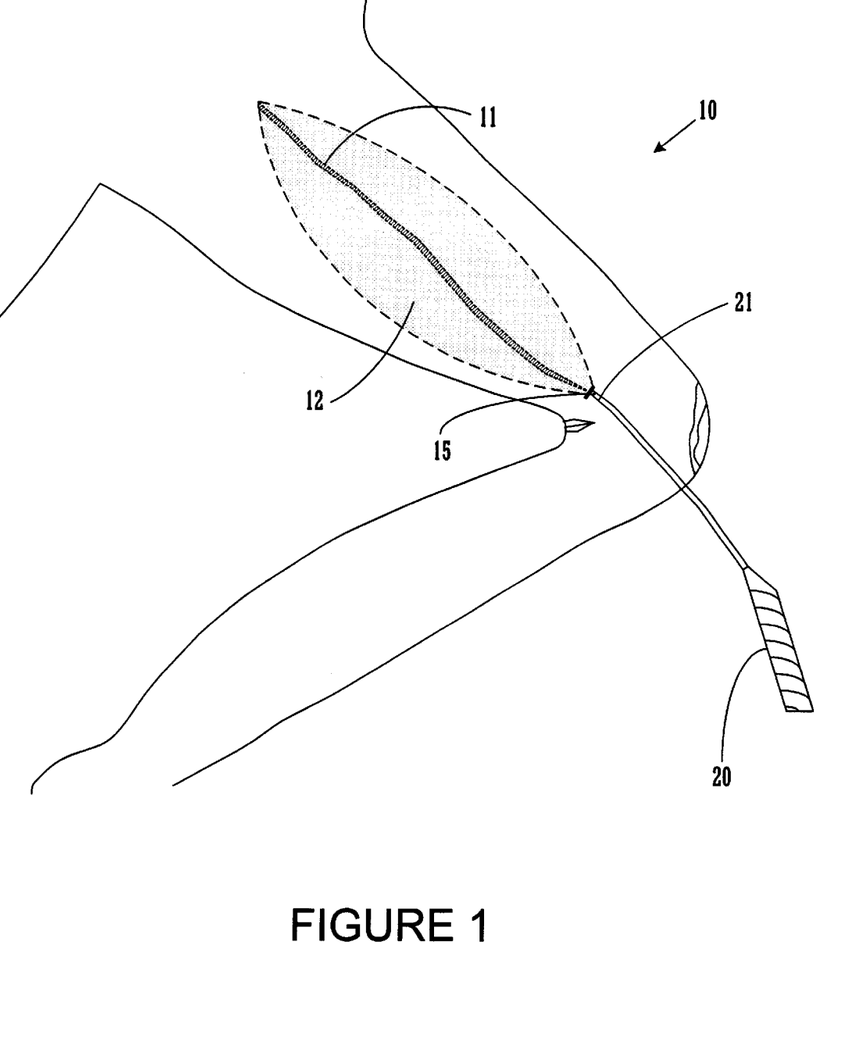
FIG. 1 is a top view of a patient's leg and an infusion cannula used to infuse a solution into tissue adjacent a saphenous vein to be harvested according to an embodiment of the invention.

Referring to FIG. 1, a patient's leg 10 is illustrated in preparation for a saphenous vein graft harvesting procedure. An infusion cannula 20 comprising a hollow needle tip 21 is inserted into a small incision 15 made in the inner thigh of the patient's leg 10 near the knee. A solution of fluid is delivered through the hollow needle tip 21 of the infusion catheter 20 and is infused into a volume 12 of tissue within the subcutaneous layer 17 between the skin layer 16 and the muscle fascia 18 (FIG. 3), and surrounding the saphenous vein 11 to be harvested. The volume 12 of tissue to be infused is determined by the amount of vein to be harvested. For example, in some situations, the harvesting of the vein may continue through to the lower limb of the leg. In general, the volume 12 of infusion should include the area surrounding the portion of the vein to be harvested. Suitable isotonic solutions may be used for infusion, for example, saline or ringer's lactate, with the optional addition of epinephrine or xylocaine. The amount of solution may vary depending upon the size of the patient and the area to be infused. Varying degrees of solution infusion are possible while keeping in mind that the infused solution attenuates the ultrasonic energy heating to protect the tissue and provides a greater hydration effect. The fluid is preferably warmed to body temperature and is infused in the subcutaneous tissue 17 along the course of the saphenous vein 11 to the point of fullness. In one embodiment of the procedure the solution comprises a wetting solution including approximately 200 cc's to 250 cc's of normal saline to which 10 cc's of 1% xylocaine with epinephrine 1:100,000 to be injected into the medial thigh subcutaneous space.

Figure 2:
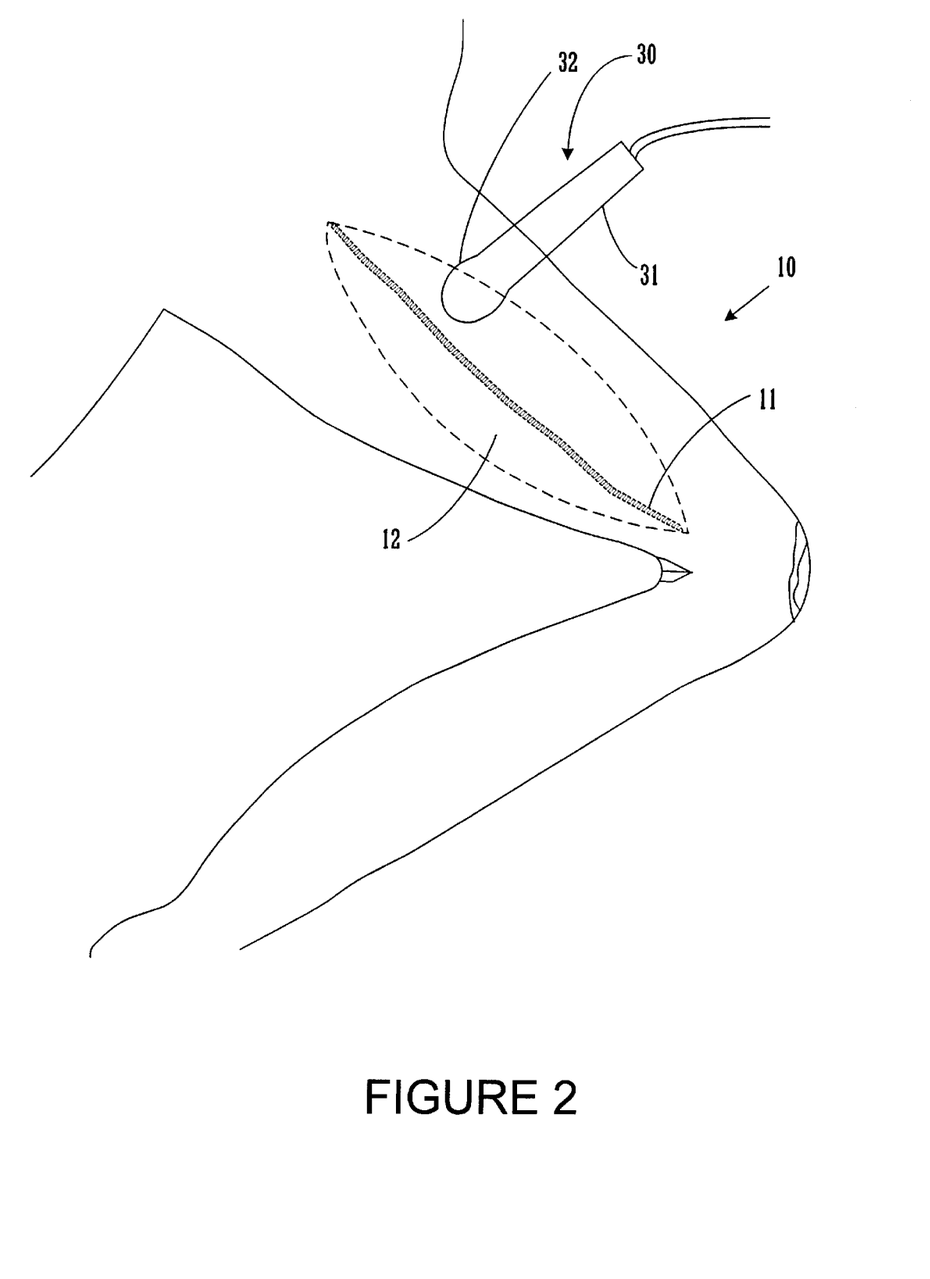
FIG. 2 is a top view of the patient's leg of FIG. 1 and an energy transducer used to warm the infused tissue.
Figure 3:
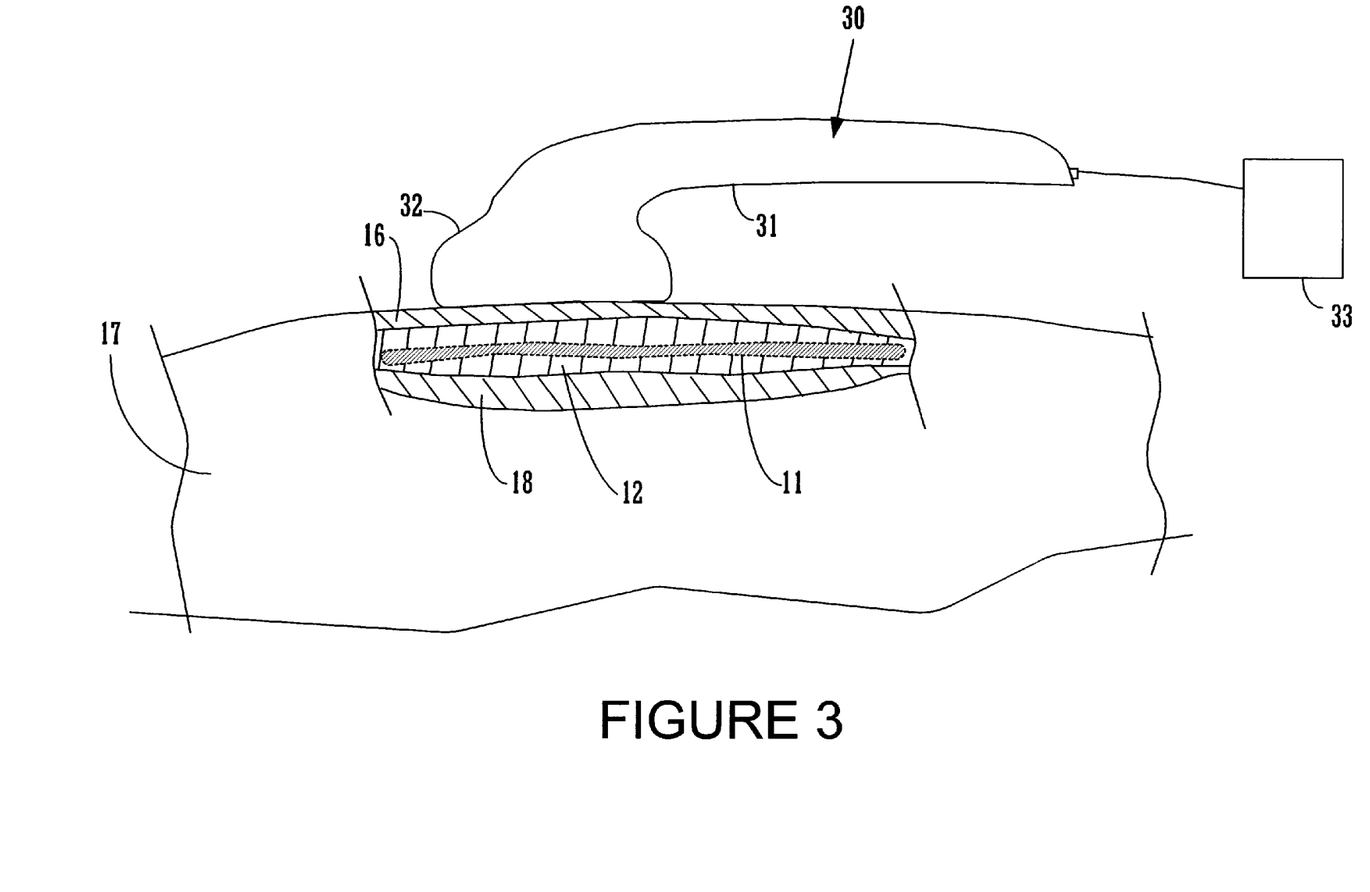
FIG. 3 is a side partial cross sectional view of the patient's leg and an energy transducer of FIG. 2.
Figure 4:
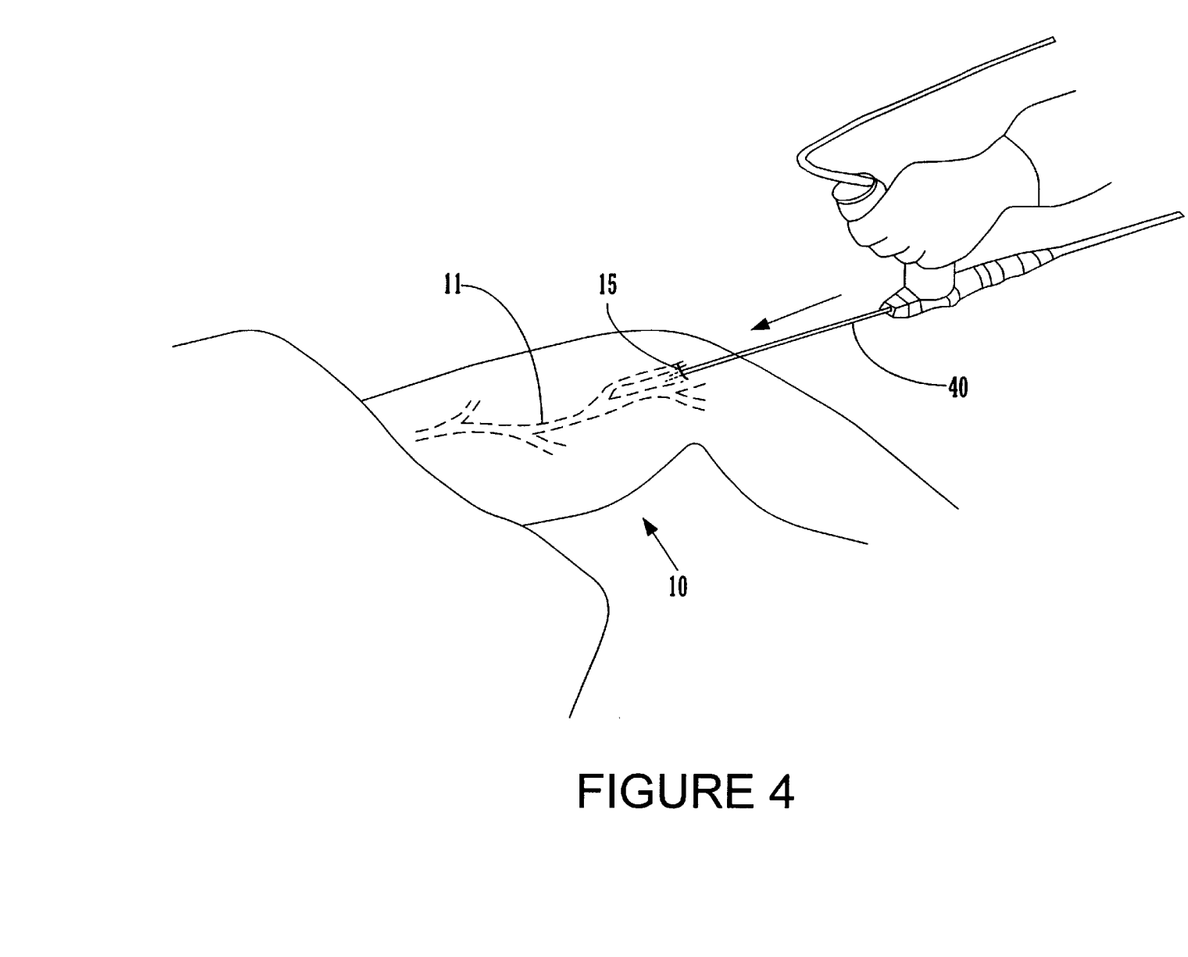
FIG. 4 is a perspective view of an endoscopic instrument in use in preparing the vein for removal.
Figure 5:
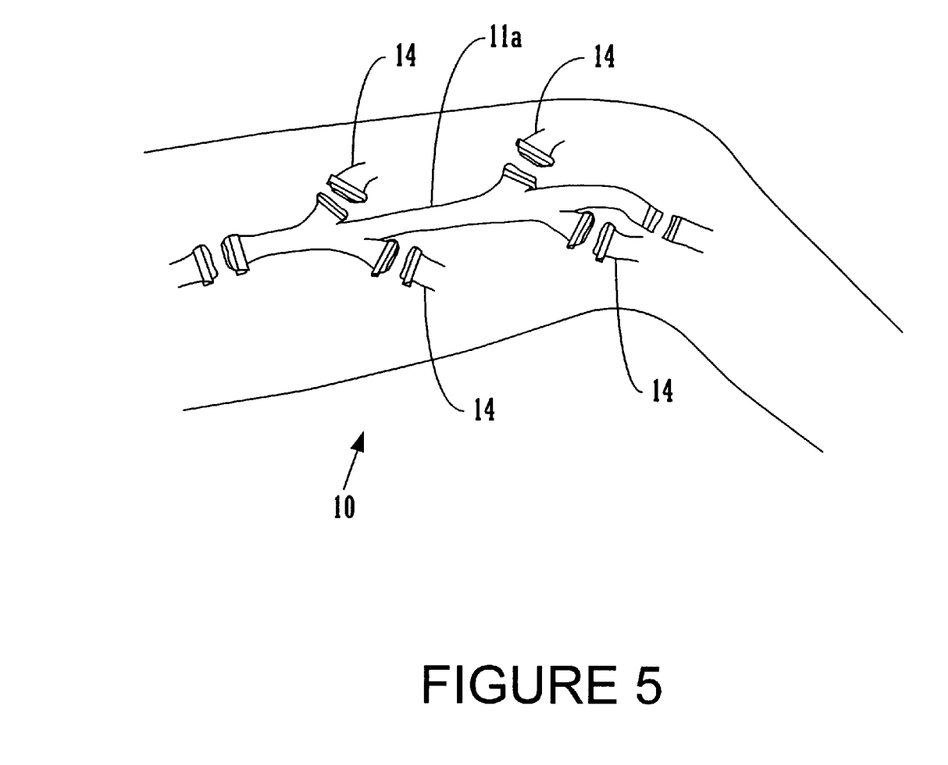
FIG. 5 is a top perspective view of the saphenous vein after being ligated, separated from the surrounding tissue and transected for removal.

As illustrated in FIGS. 2 and 3, after the wetting solution is infused, an ultrasonic instrument 30 comprising a handle 31 coupled to a power source 33, and an ultrasonic transducer head 32 (protected by a sterile sheath) is used to apply ultrasonic energy though the skin 16 of the patient's leg 10, to the volume 12 of tissue surrounding the saphenous vein 11. Preferably the ultrasonic transducer 32 comprises crystals embedded in a polymer, such as, for example, a lead zirconate titanate crystals embedded in acrylate, that diffuses the energy relatively more superficially than other transducers. A transmitting gel is applied to the skin 16 to provide coupling between the ultrasonic transducer 32 and tissue of the patient for efficient transmission of the ultrasonic waves. The provider holds the instrument 30 by the handle 31 and applies the transducer head 32 to the patient's skin, moving the transducer through out the area of skin corresponding to the volume 12 of tissue beneath the skin to be treated. In one embodiment, an ultrasonic field is introduced into the tissue through the skin at a frequency of 1 MHz and a power density of 3 watts/cm2 for a sufficient time for the tissues to become warm and soft generally about 2–5 minutes. Preferably an ultrasonic frequency of about 0.5 to 5 MHz is used with a power density ranging from about 2.5 to 4 watts/cm2. The application of the ultrasonic energy is believed to cause cavitation and microstreaming, i.e., the movement of the fluid in a linear direction away from the ultrasonic energy source. The result is the loosening of the tissue surrounding the blood vessel. The tissue infused with the solution also becomes super-hydrated upon application of the energy As illustrated in FIG. 4 an endoscope and associated instruments 40 are placed through the incision 15. The endoscope and associated instruments 40 are used to separate the surrounding tissue from the saphenous vein 11 to provide a working area for ligating the tributary vessels and to permit removal of the vein 11 without significant tearing or damage to the vessel and surrounding tissue as it is removed. The tributary vessels 14 are ligated and then the main vessel 11a is transected and removed. Various methods of tissue separation, dissection, ligation and transection may be used. Such procedures are generally know and may further develop. Examples of various methods are described in U.S. Pat. Nos. 5,928,138 and 6,277,137 incorporated herein by reference. As illustrated in FIG. 5, a main portion 11a of a saphenous vein 11 has been ligated and transected from the tributary vessels 14 and is ready for removal.

The tissue preparation technique may also be used in an open saphenous vein graft harvesting procedure and is also useful when an endoscopic procedure is converted to an open procedure. The tissue is prepared in the same manner as described with respect to FIGS. 1–3. The incision is then made along the length of the inner thigh where the vessel is to be removed. The harvesting procedure is performed in a typical known manner. The open procedure is made easier, not only because the tissue separation is easier, but also because the ultrasonic treatment in combination with the infusion of the fluid super-hydrates the tissue, lessening the effects of tissue dehydration from exposure of the fatty and other tissue to air.

Figure 6:
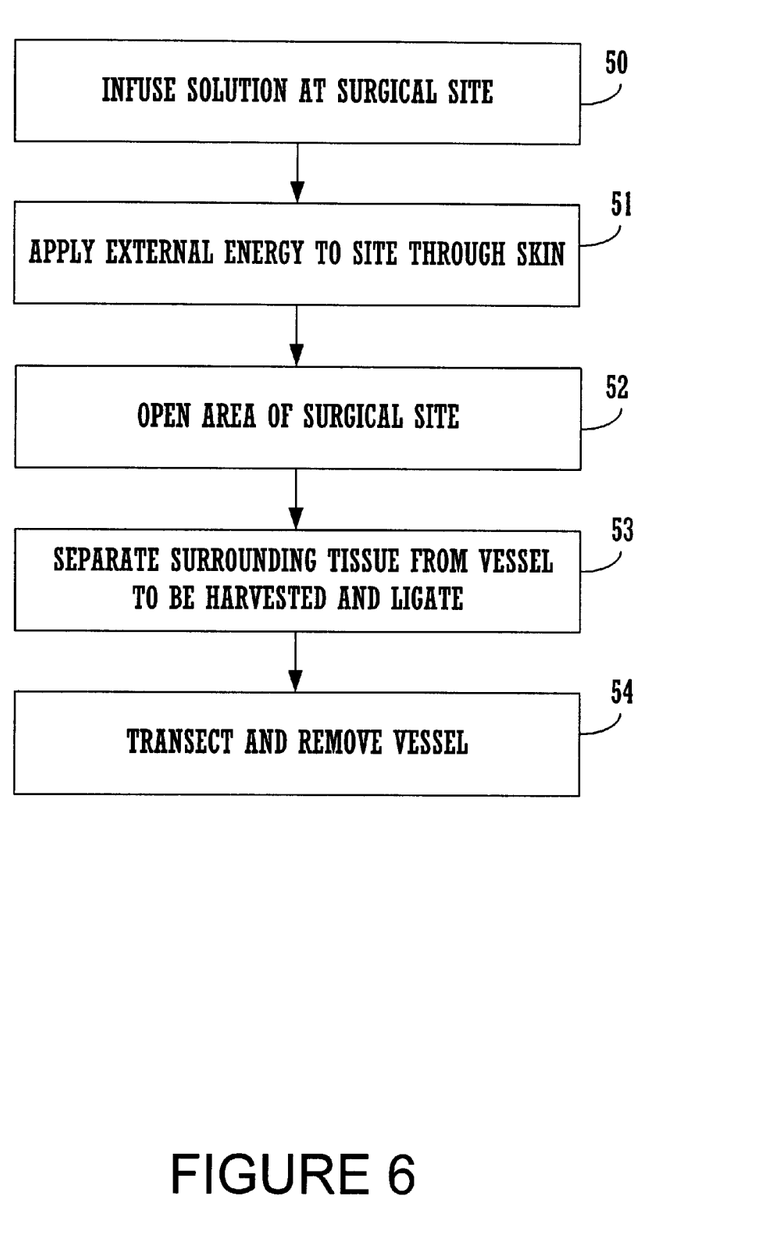
FIG. 6 is a schematic of the method of preparing and harvesting a vessel according to an embodiment of the invention.

FIG. 6 is a schematic of a method of saphenous vein graft harvesting using an open procedure. First the surgical site is prepared by infusion solution into the tissue around the vein (50). An energy transducer is used to deliver energy through the skin to the tissue that has been infused. (51). Alternative energy sources may be used such as other acoustic waves that heat the tissue with pressure from the sound waves, and electromagnetic radiation, such as e.g. light, columnated light, laser or radio frequency energy that is used in a manner that minimizes cell damage while it loosens the intra cellular adhesions and connections. Once treated with the energy, the incision is made opening the area of the surgical site to access the saphenous vein (52). The open procedure is then accomplished by separating the surrounding tissue from the vessel to be harvested and ligating the tributary vessels. (53). Finally, the vessel is transected and removed (54).

Figure 7:
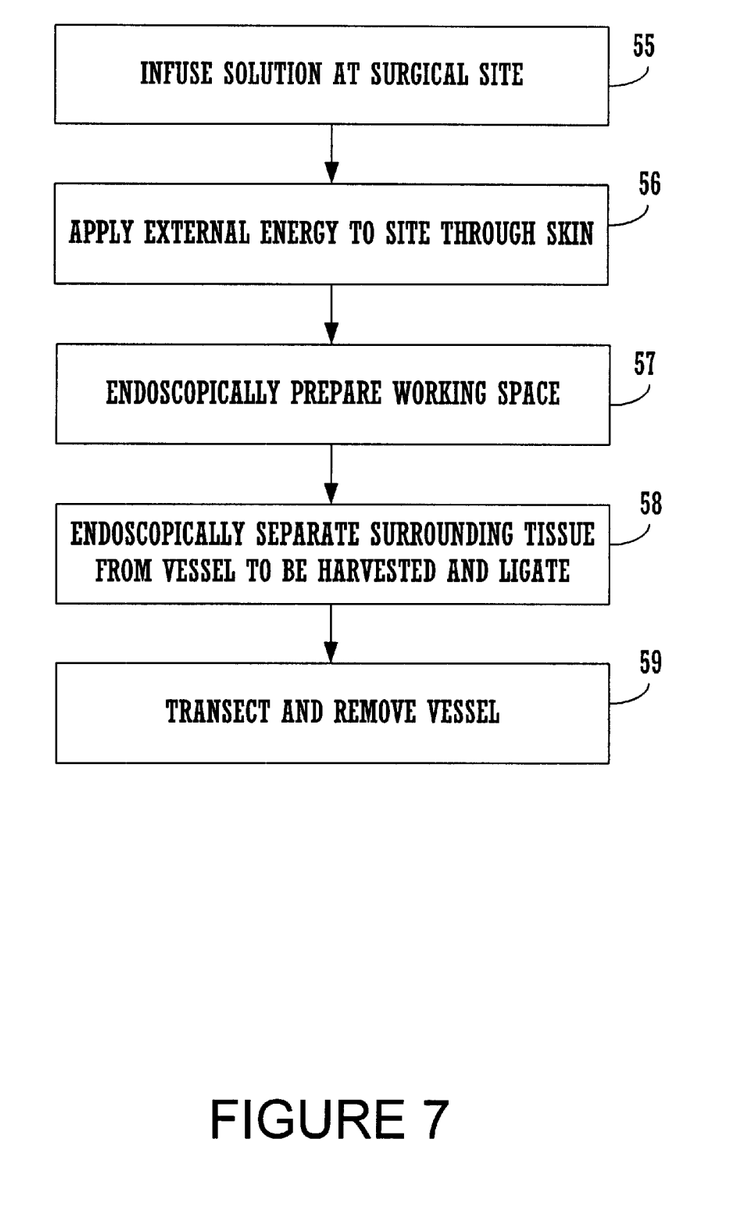
FIG. 7 is a schematic of the method of preparing and endoscopically harvesting a vessel according to another embodiment of the invention.

FIG. 7 is a schematic of a method of saphenous vein graft harvesting using an endoscopic procedure. The surgical site is prepared by infusing a solution into the tissue around the portion of the vein to be harvested (55). An external energy, e.g., ultrasound is applied through the skin and through the infused tissue to loosen the intercellular connections between the vein and the surrounding tissue (56). Instruments with visualization features (endoscopic or optical instruments) are used to prepare a working space along the saphenous vein (57). In doing so or as a later step, tissue is endoscopically separated from the tissue surrounding the vessel to be harvested and the tributary vessels are ligated (58). The vessel to be harvested is then transected and removed from the leg (59).

While the invention has been described with reference to particular embodiments, it will be understood to one skilled in the art that variations and modifications may be made in form and detail without departing from the spirit and scope of the invention. Such modifications may include substituting other elements, components or structures that the invention can be practiced with modification within the scope of the following claims.

What is claimed is:

1. A method for removing a portion of vessel from a patient's body comprising the steps of:
    infusing a solution into a volume of tissue surrounding a portion of the vessel to be removed;
    applying energy to the volume of tissue by way of a device external to the body interfacing with the patient's skin, to loosen the intercellular bonds between the portion of the vessel to be removed and the tissue surrounding the portion of the vessel;
    separating the tissue surrounding the portion of the vessel from the vessel, ligating the portion of the vessel and transecting the portion of the vessel to be removed from remaining portions of the vessels.

2. The method of claim 1 wherein the step of infusing a solution comprises infusing a solution in a subcutaneaous layer of the patient's body.

3. The method of claim 2 wherein power density of the ultrasonic vibrations is about 2.5 to 4 watts per $cm^2$.

4. The method of claim 1 wherein the step of applying an energy to the tissue comprises applying ultrasonic vibrations through the skin of the patient with an ultrasonic instrument comprising a handle and a transducer head.

5. The method of claim 3 wherein the step of applying an energy further applying the energy through a transducer head having a plurality of crystals embedded in a polymer.

6. The method of claim 4 wherein the step of applying an energy further comprises applying the energy through a transducer head having a plurality of lead zirconate titanate crystals.

7. The method of claim 3 wherein the ultrasonic vibrations are applied at a frequency of between about 0.5 to 5 MHz.

8. The method of claim 1 wherein the step of applying energy to the volume of tissue comprises applying electromagnetic energy to the tissue through the skin.

9. The method of claim 8 wherein the step of applying electromagnetic energy comprises applying a laser energy to the tissue through the skin.

10. The method of claim 1 wherein the step of separating the volume of tissue comprises endoscopically separating the surrounding tissue from the portion of the vessel.

11. The method of claim 1 wherein the step of ligating the tissue comprises endoscopically ligating tributary vessel branching off from the portion of the vessel to be removed.

12. The method of claim 1 wherein the steps of injecting the solution and applying energy comprises hydrating the tissue to reduce dehydration of the tissue during an open surgical procedure.

13. A method for harvesting a portion of a vessel from a patient's body comprising the steps of:
    infusing a solution into a volume of tissue surrounding a portion of the vessel to be harvested;
    applying an energy to the volume of tissue by way of a device external to the body interfacing with the patient's skin, to loosen the intercellular bonds between the portion of the vessel to be harvested and the tissue surrounding the portion of the vessel;
    separating the tissue surrounding the portion of the vessel from the vessel, ligating the portion of the vessel and transecting the portion of the vessel to be harvested from remaining portions of the vessels.

14. The method of claim 13 wherein the vessel is a saphenous vein graft.

15. The method of claim 13 wherein the step of applying an energy to the volume of tissue comprises applying ultrasonic vibrations through the skin of the patient with an ultrasonic instrument comprising a handle and a transducer head.

16. The method of claim 15 wherein the step of applying an energy further comprises applying the energy through a transducer head having a plurality of crystals embedded in a polymer.

17. The method of claim 16 wherein the step of applying an energy further comprises applying the energy through a transducer head having a plurality of lead zirconate titanate crystals.

18. The method of claim 15 wherein the ultrasonic vibrations are applied at a frequency of between about 0.5 to 5 MHz.

19. The method of claim 15 wherein the power density of the ultrasonic vibrations are about 2.5 to 4 watts per $cm^2$.

20. The method of claim 13 wherein the step of applying energy to the volume of tissue comprises applying electromagnetic energy to the volume of tissue through the skin.

21. The method of claim 20 wherein the step of applying electromagnetic energy comprises applying a laser energy to the volume of tissue through the skin.

22. The method of claim 13 wherein the step of separating the volume of tissue comprises endoscopically separating the surrounding tissue from the portion of the vessel.

23. The method of claim 13 wherein the steps of injecting the solution and applying energy comprises hydrating the volume of tissue to reduce dehydration of the volume of tissue during an open surgical procedure.

* * * * *